United States Patent [19]

Rupchock et al.

[11] 4,376,828

[45] Mar. 15, 1983

[54] BILIRUBIN TEST KIT

[75] Inventors: Patricia A. Rupchock; Arthur C. Skjold, both of Elkhart, Ind.

[73] Assignee: Miles Laboratories, Inc., Elkhart, Ind.

[21] Appl. No.: 294,570

[22] Filed: Aug. 20, 1981

[51] Int. Cl.³ ............................................. G01N 33/72
[52] U.S. Cl. ....................................... 436/97; 422/61; 422/69; 436/178; 436/903
[58] Field of Search ................... 23/230 B, 905, 929; 422/56, 57, 55, 61, 69

[56] References Cited

U.S. PATENT DOCUMENTS

| | | | |
|---|---|---|---|
| 2,854,317 | 9/1958 | Free et al. | 23/230 B |
| 3,672,845 | 6/1972 | Verbeck | 422/57 |
| 3,847,553 | 11/1974 | Verbeck | 422/56 |
| 3,915,647 | 10/1975 | Wright | 422/68 X |
| 4,038,031 | 7/1977 | Lam | 422/56 X |
| 4,168,146 | 9/1979 | Grubb et al. | 23/230 B |
| 4,301,027 | 11/1981 | Blumcke et al. | 422/56 X |

Primary Examiner—Arnold Turk
Attorney, Agent, or Firm—Edward H. Gorman, Jr.

[57] ABSTRACT

A test kit for the determination of bilirubin in a test sample is disclosed. It comprises a reagent capable of producing a color change or other detectable response in the presence of bilirubin, and a test mat comprising finely divided silica gel. The kit is utilized by wetting the test mat with a portion of a liquid test sample suspected of containing bilirubin, contacting the wetted mat with the reagent, causing the reagent to at least partially wet the mat and observing the appearance of a color change or other detectable response.

11 Claims, No Drawings

BILIRUBIN TEST KIT

BACKGROUND OF THE INVENTION

1. Field of the Invention

The presently disclosed invention relates to the analysis of bilirubin in a test sample. More particularly, it relates to an improved test kit of the test mat/reagent tablet format for use in bilirubin determination.

The chemistry and biology of the bile pigments are quite complicated; some of the steps in the metabolic pathways being still shrouded in mystery. Much of the older literature on the subject is now obsolete, and not of primary concern to the clinical chemist. Bilirubin, however, is one of the bile pigments occurring somewhat early in the metabolism of heme, and substantial analytical literature is available.

Bilirubin originates primarily from the breakdown of the heme moiety of hemoglobin in senescent erythrocytes by the reticulo-endothelial system. This occurs primarily in the spleen, liver and bone marrow.

Bilirubin which is formed from the breakdown of hemoglobin is transported in the plasma bound to a carrier such as albumin or, in small amounts, $\alpha$-globulins and other serum proteins. Anionic drugs, such as salicylates and sulfa, or other anions, such as free fatty acids, can compete for these binding sites and substantially reduce the bilirubin transport capacity of the plasma. It is hypothesized that bilirubin dissociates from its carrier protein in the liver cell membrane, and it is transported intracellularly by some act or process, either unbound or attached to high-affinity, specific acceptor systems.

Conjugation of bilirubin with glucuronic acid and, to a lesser extent with sulfuric and possibly other acids, occurs in the liver. Conjugated bilirubin is excreted from the liver cell into the bile canaliculus. In the intestinal tract a small fraction of the conjugated bilirubin excreted in the bile is hydrolyzed and the unconjugated bilirubin reabsorbed. Consequently, practically all excreted bilirubin is in the conjugated form.

The diagnostic value of determining bilirubin in urine has long been recognized. Normal urinary bilirubin levels are less than about 0.05 milligrams per deciliter (mg%). Accordingly, elevated bilirubin levels in urine connote the possible existence of a pathological condition in a patient. For example, high bilirubin levels can result from biliary obstruction, and hemolytic and hepatic disease. It is generally recognized that the presence of bilirubin in urine at concentrations greater than the above mentioned 0.05 mg% indicates the desirability of performing more comprehensive diagnostic procedures determinative of the specific pathological condition causing the elevated urinary bilirubin concentration.

As stated supra, essentially all bilirubin appearing in pathological urines or other bodily excreta is in the glucuronate conjugated form. Many analytical systems exist in the art for determining this form of bilirubin.

The preparation and use of a bilirubin test device is described in detail in U.S. Pat. No. 3,585,001. While the test devices which have been described in the art provide very rapid and convenient means for detecting urinary bilirubin, it is generally known that the available test devices are not sufficiently sensitive to detect levels of bilirubin only slightly elevated from the normal level, i.e., between 0.1 and 0.4 mg% bilirubin.

There have been a few reported attempts to increase the sensitivity of the reaction between diazonium compounds and urinary bilirubin; however, the test systems that have resulted have certain disadvantages. U.S. Pat. No. 3,880,588 describes a class of diazonium compounds designed to enhance the colorimetric response of the azobilirubin complex and to decrease interfering color reactions with urobilinogen, which is structurally and chemically very similar to bilirubin. The described diazonium compounds, unlike the conventional compounds, form interfering colored products with such constituents of urine as homogentisic acid and 5-hydroxyindole-3-acetic acid. The latter is a normal constituent of urine and as little as 1 mg% of such constituent in urine causes false positive results using the diazonium compounds described in this patent.

Another attempt to increase the sensitivity of the test device-incorporated diazonium reagents is described in U.S. Pat. No. 3,853,476 which discloses the use of certain phosphoric acid diesters as sensitizing or potentiating agents for the reaction between the diazonium compound and bilirubin. However, due to the incompatibility between the phosphoric acid diesters and aqueous media, test devices prepared according to this patent must be manufactured by a double-impregnation process.

It should be mentioned that various so-called "accelerating agents" have been described in the art relative to the detection of bilirubin in serum by the diazo-coupling reaction. Such agents have included caffeine, dyphylline, sodium acetate, sodium benzoate, gum arabic, and various other chemically unrelated compounds.

2. Description of the Prior Art

Over 70 tests have been proposed for the qualitative determination of bilirubin in urine. In general, these can be grouped into four categories depending on the principle used: (a) observation of the color of the urine sample; (b) the titration of the urine sample with a dye (e.g., methylene blue) until the dye color dominates over the bilirubin color; (c) oxidation of bilirubin to characteristic colors; and (d) diazo-coupling. Most of those tests which are clinically feasible rely on diazo-coupling.

Bilirubin, in the presence of certain diazonium compounds, cleaves at its central methylene group to form two molecules of pigment known as azobilirubin. These molecules appear blue to purple at acid and basic pH and red at neutral pH. The reaction can be visualized structurally as follows:

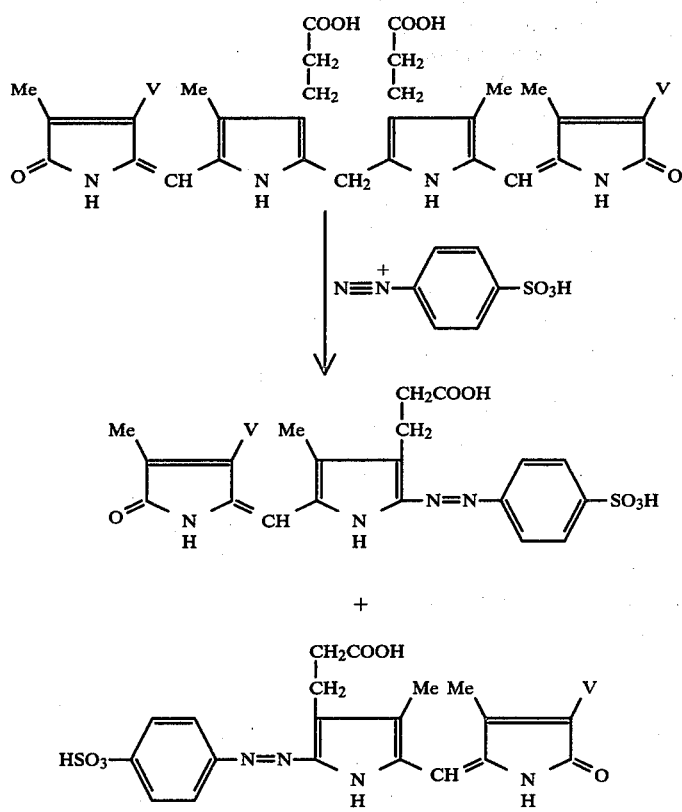

where Me is methyl and V is vinyl.

In 1953, Free and Free introduced a tablet test utilizing the diazo-coupling technique in surprisingly convenient form. This test is available commerically as ICTOTEST ® by the Ames Division of Miles Laboratories, Inc. (See Free et al., Gastroenterology, 24, 414 (1953); and U.S. Pat. No. 2,854,317, issued to Free et al. on Sept. 30, 1958.)

ICTOTEST utilizes a test mat capable of absorbing an aqueous test sample, while adsorbing bilirubin which is present, thereby concentrating the analyte. Subsequent to applying several drops of test sample to a spot on the test mat, a reagent tablet containing a stabilized, buffered diazonium reagent composition is placed over the wetted area of the test mat. The tablet is then "flooded" with a few drops of water, thereby partially dissolving the reagents and contacting any adsorbed bilirubin with the diazonium salt-laden solution. If the test sample contains bilirubin a purple color develops in the test mat. This test has been found to be sensitive at bilirubin concentrations as low as 0.05 to 0.10 mg%.

It is to improving ICTOTEST that the present invention relates, and in particular, to improving the test mat. Free et al. teach the use of an asbestos-containing cellulose as the preferred composition for a test mat. Asbestos has the property of being especially suited to adsorbing bilirubin, while absorbing aqueous test samples. However, reference to "The Merck Index", 9th ed., P.110, Merck & Co., Inc. (1976), reveals that asbestos has associated with it potentially serious health hazards. Moreover, alternatives to asbestos suggested by Free et al., which includes Celite (silicon dioxide) and clays have associated with them their own attendant potential health hazards while not possessing sufficient aqueous absorbance coupled with bilirubin adsorbance.

Accordingly, the present invention is the culmination of an attempt to find materials for use in formulating a test mat which, while capable of adsorbing bilirubin to a high degree and otherwise fulfilling the requirements of the ICTOTEST test mat, nevertheless do not embody the hazardous drawbacks attendant asbestos and silicon dioxide. It is this twofold requirement of a test mat—a high degree of absorbance for an aqueous test sample, thereby permitting relatively large sample inoculation at a single point on the mat; coupled with a likewise high propensity to adsorb bilirubin, thereby concentrating it at the point of inoculation—that renders the invention unique.

SUMMARY OF THE INVENTION

Briefly stated, the present invention is a test kit for determining the presence of bilirubin in a test sample. The kit comprises a reagent capable of providing a detectable response to the presence of bilirubin, and a test mat to which the test sample and the reagent are sequentially applied. The test mat comprises finely divided silica gel. Moreover, the invention resides in a method for determining bilirubin in a test sample by utilizing the test kit.

DETAILED DESCRIPTION OF THE INVENTION

The cornerstone of the invention is the improved test mat, or rather, its improved composition. It has been found that finely divided silica gel, despite teachings in the art directly to the contrary, is capable of concentrating bilirubin at the site of application of a bilirubin-containing aqueous test sample, while permitting the rest of the sample to diffuse away.

Chemically, silica gel is a precipitated silicate having the approximate empirical formula $H_2SiO_3$[1]. It is presently believed to comprise a polymerized silica, i.e., a condensation product of silicic acid.[2] It is prepared from an aqueous silicate solution by acidification, subsequent washing to remove electrolytes, and drying to various degrees of anhydrousness.[3] The resultant solid is generally considered to be a three-dimensional crosslinking of hydrated silica micelles.[4] It adsorbs water readily, and is used to dry blast furnace gases, air and other gases[5], including hydrocarbons. "Since silica gel has a greater affinity for water than for hydrocarbons, water adsorbed from [a hydrocarbon stream] will gradually displace all hydrocarbons".[6]

[1] "Merck Index", 9th ed., p. 1099, Merck & Co., Inc. Rahway, N.J. (1976).
[2] Kirk-Othmer, "Encyclopedia of Chemical Technology", 18, 61–70, John Wiley & Sons (1969).
[3] Ibid.
[4] Ibid.
[5] "Hackh's Chemical Dictionary", 4th ed., p. 610, McGraw Hill, Inc. (1972)
[6] Kirk-Othmer, op cit.

In view of the latter characteristic of silica gel to bind (adsorb) water more tightly than hydrocarbons, it is indeed surprising to find that in the present invention *it binds bilirubin while permitting water to flow through it.*

In view of the teachings of Kirk-Othmer, one skilled in the art would expect that once a silica gel test mat became saturated with adsorbed water molecules, any bilirubin present in the test sample would merely flow away from the point of sample application, carried along by excess water. Surprisingly, the exact opposite phenomenon occurs.

It has been found that the test mat of the present invention should contain silica gel which is finely divided in order to perform optimally. That is to say, it should be of a particle size ranging from $5\mu$ (microns) or smaller to about $200\mu$. It is presently especially preferred to utilize silica gel having a particle size range of about $5\mu$ to about $20\mu$.

The amount of silica gel present in the test mat is not critical. It can vary from about 100 percent, as in the case of a thin layer chromatography (TLC) plate having a 2 millimeter layer of silica gel, to much smaller amounts such as a polyvinyl chloride microporous membrane which contains relatively small amounts of finely divided silica gel. The optimum amount of silica gel to use in the test mat can easily be determined by routine experiments such as those presented below in the Examples. It is influenced by such parameters as the volume of test sample available, and the sensitivity desired for the analysis.

Not only can the amounts and particle size of the silica gel in the test mat vary widely, but the nature of other ingredients which may be present can be equally diverse. For example, if the test mat is to be a TLC plate, it might contain a small amount of an inert binder to secure the silica gel particles to a support member—in this case a glass plate. It follows that other materials can comprise the support member in lieu of glass, such as a polystyrene, nylon or polypropylene sheet.

Moreover, the silica gel can be integrally combined with, or embedded in, a support member. For example, it can be mixed with softened or melted polyvinyl chloride and later extruded into a homogeneous film. Alternatively, it can be combined with fibrous material such as cellulose or paper and formed into a test mat.

The test kit presently claimed includes, in addition to the test mat which concentrates the bilirubin, a reagent capable of detecting the concentrated bilirubin. By "reagent" is meant any system of one or more components which interacts with bilirubin to produce a detectable response, such as the appearance of or change in color, a change in ultraviolet light reflectance or absorption, fluorescence, or other physically discernible manifestation. The reagent can be one which produces a chemical change, such as the stabilized diazonium salt/buffer combination described in the aforementioned Free et al. U.S. Pat. No. 2,854,317, which is herein incorporated by reference; or the tablet currently included with the ICTOTEST test kit. It can be an immunogenic system such as an antibody and antigen-labeled conjugate which provide a response in the presence of bilirubin; it can be a system which becomes fluorescent or luminescent in the presence of bilirubin. Presently preferred as a reagent is a diazonium salt/acid buffer combination. Especially preferred is the ICTOTEST tablet which contains p-nitrobenzenediazonium-p-toluenesulfonate, salicylic acid, and an effervescent base.

In use, a portion of a test sample suspected of containing bilirubin, such as urine, is applied to the test mat at a discrete point. The reagent is then applied to the moistened area of the mat and caused to at least partially dissolve in solvent and wet the test mat, which is then observed, either visually or instrumentally, for the appearance of a detectable response. Where the reagent is based on the bilirubin/buffered diazonium salt interaction, a positive response is the appearance of color—usually red to purple.

EXAMPLES

The following examples describe experiments performed in developing the present invention. While they illustrate preferred embodiments and the inventors' concept of the best mode of making and using the invention, they are in no way to be interpreted as limiting its scope.

EXAMPLE I

PVC Impregnated With Silica Gel

A test kit was prepared for the determination of the presence of bilirubin in urine. It consisted of a reagent tablet and a test mat formulated from PVC impregnated with silica gel. The reagent comprises a tablet obtained from an ICTOTEST test kit (Ames Division, Miles Laboratories, Inc.).

The test mat was prepared from Microporous Membrane Grade A-40 polyvinylchloride (Amerace Corp.).

The membrane was washed in a solution containing 5 g (grams) sulfosalicylic acid per 100 ml distilled water until purple color was removed. The membrane was then rinsed with deionized water and dried at 60° C. for about 10 minutes in an air oven. The thus-treated membrane was cut to form square test mats measuring about one inch on a side. At a discrete point of each of five mats was added, respectively, two drops of urine containing the following amounts of bilirubin: 0 (control), 0.05, 0.1, 0.2 and 0.4 mg%. An ICTOTEST tablet was placed on each square. Two drops of water were placed on each tablet and allowed to fall onto the respective mat. After 20 to 30 seconds the mats were observed for color formation. No color formed on the mats containing 0 and 0.05 mg% bilirubin, whereas colors appeared on the other mats ranging from very light purple at 0.1 mg% to light-medium purple at 0.4 mg%.

The experiment shows the efficacy of a silica gel-containing polyvinylchloride microporous membrane in determining the presence of bilirubin in a test sample.

EXAMPLE II

TLC Plates Of Silica Gel

An experiment was conducted to prepare a test kit for assaying bilirubin using TLC plates of finely divided silica gel as a test mat.

TLC plates were obtained from Merck & Co. They comprised square glass plates measuring 20 cm (centimeters) on a side, one face of which had been coated with finely divided silica gel having a particle size range of 10 to 15μ. The silica gel layer was about 2 mm (millimeters) in thickness. The plates were washed with a 5% solution of sulfosalicylic acid, similarly as in Example I, until purple color was removed, then rinsed with deionized water. The rinsed plates were dried at room temperature over night on the laboratory bench.

One of the dried plates was portioned off such that the silica gel coating was divided into one inch squares. As in Example I, five of the squares were individually inoculated at discrete points with urine containing successively increasing amounts of bilirubin: 0 (control), 0.5, 0.1, 0.2 and 0.4 mg%. Each square was inoculated with five drops of the respective urine. An ICTOTEST tablet was placed over each moistened square and treated with 2 drops of deionized water, which was permitted to fall onto the square. After 20–30 seconds, the squares were examined for the appearance of color. No change in color was observed for the control, whereas colors appeared on the other squares ranging from very light purple for the 0.05 mg% urinary bilirubin to a medium purple for the 0.4 mg% sample.

This experiment illustrates the efficacy of a finely divided silica gel-coated TLC plate as a test mat for the present invention.

What is claimed is:

1. In a test kit for determining the presence of bilirubin in a test sample, wherein the kit comprises a reagent capable of producing a detectable response in the presence of bilirubin, and a test mat capable of absorbing at least a portion of the test sample, the improvement wherein said test mat comprises finely divided silica gel.

2. The improvement of claim 1 wherein the test mat is a microporous film of polyvinylchloride containing finely divided silica gel.

3. The improvement of claim 1 wherein the test mat is a thin layer of finely divided silica gel affixed to a support member.

4. The improvement of any of claims 1–3 wherein the finely divided silica gel has a particle size range of from about 5 to about 200 microns.

5. A method for determining the presence of bilirubin in a test sample comprising the steps of wetting a discrete point of a test mat comprising finely divided silica gel with a portion of the test sample, placing onto the wetted portion of the mat a reagent capable of producing a detectable response in the presence of bilirubin and causing the reagent to at least partially dissolve in a solvent and wet the test mat, and observing the appearance of the detectable response.

6. The method of claim 5 wherein the reagent is in the form of a tablet.

7. The method of claim 5 or 6 wherein the test mat is a microporous film of polyvinyl chloride containing finely divided silica gel.

8. The method of claim 5 or 6 wherein the test mat is a thin layer of finely divided silica gel affixed to a support member.

9. The method of any of claims 5 or 6 wherein the finely divided silica gel has a particle size of from about 5 to about 200 microns.

10. The method of claim 5 or 6 wherein the test mat is a microporous film of polyvinyl chloride containing finely divided silica gel, the silica gel having a particle size of from about 5 to about 200 microns.

11. The method of claim 5 or 6 wherein the test mat is a thin layer of finely divided silica gel affixed to a support member, the silica gel having a particle size of from about 5 to about 200 microns.

* * * * *